(12) United States Patent
Wabnitz et al.

(10) Patent No.: US 8,168,807 B2
(45) Date of Patent: May 1, 2012

(54) PROCESS FOR ONE-STAGE PREPARATION OF 2-METHYLTETRAHYDROFURAN FROM FURFURAL OVER TWO CATALYSTS IN A STRUCTURED BED

(75) Inventors: Tobias Wabnitz, Mannheim (DE); Daniel Breuninger, Bobenheim-Roxheim (DE); Jens Heimann, Worms (DE); Rene Backes, Lampertheim (DE); Rolf Pinkos, Bad Duerkheim (DE)

(73) Assignee: BASF SE, Ludwigshafen (DE)

( * ) Notice: Subject to any disclaimer, the term of this patent is extended or adjusted under 35 U.S.C. 154(b) by 485 days.

(21) Appl. No.: 12/442,877

(22) PCT Filed: Jun. 24, 2008

(86) PCT No.: PCT/EP2008/058038
§ 371 (c)(1),
(2), (4) Date: Mar. 25, 2009

(87) PCT Pub. No.: WO2009/003881
PCT Pub. Date: Jan. 8, 2009

(65) Prior Publication Data
US 2010/0048922 A1      Feb. 25, 2010

(30) Foreign Application Priority Data
Jul. 2, 2007   (EP) .................................. 07111508

(51) Int. Cl.
*C07D 307/89*    (2006.01)
(52) U.S. Cl. ...................................................... 549/429
(58) Field of Classification Search .................. 549/429
See application file for complete search history.

(56) References Cited

U.S. PATENT DOCUMENTS 6,479,677 B1    11/2002   Ahmed
2003/0018205 A1   1/2003   Ahmed

FOREIGN PATENT DOCUMENTS

WO    02 34697    5/2002

OTHER PUBLICATIONS

Bulenkova et al, Conversion of Heterocyclic Compounds on Membrane Catalysts .III, Hydrogenation of furfural on palladium-nickel alloy, Latvijas PSR Zinatnu Akademijas Vestis, Kimijas Serija, 1975, 6, p. 701-704 (abstract page).*
Zheng, Hong-Yan et al., "Towards understanding the reaction pathway in vapour phase hydrogenation of furfural to 2-methylfuran", Journal of Molecular Catalysis A: Chemical, vol. 246, No. 1-2, pp. 18-23, (2006).
Tsuda, Kyosuke et al., "Findings Relating the Production of Methyl-Tetrahydrofuran", J. Pharm. Soc. Jpn., Nippon Yakugakkai, Simomlyabityo and Usigomeku, vol. 66, p. 58, 1946, (with English translation).
Proskuryakov, V. A. et al., "Hydrogentation of Furfural Under Pressure", Transaction of the Lensovet Technological, Institute, Leningrad, vol. 44, pp. 3-5, 1958, (with English translation).

* cited by examiner

*Primary Examiner* — Taylor Victor Oh
(74) *Attorney, Agent, or Firm* — Oblon, Spivak, McClelland, Maier & Neustadt, L.L.P.

(57) ABSTRACT

The present invention provides a process for preparing 2-methyltetrahydrofuran by one-stage hydrogenation of furfural with a hydrogen-comprising gas in the presence of a structured bed of at least one copper catalyst and at least one catalyst which comprises at least one noble metal from groups 8, 9 and/or 10 of the periodic table of the elements applied on a support material.

20 Claims, No Drawings

PROCESS FOR ONE-STAGE PREPARATION OF 2-METHYLTETRAHYDROFURAN FROM FURFURAL OVER TWO CATALYSTS IN A STRUCTURED BED

DESCRIPTION

The present invention relates to a process for one-stage preparation of 2-methyltetrahydrofuran from furfural over at least two catalysts in a structured bed.

2-Methyltetrahydrofuran (referred to hereinafter as 2-Me-THF) is an organic solvent with high dissolution power. 2-Me-THF is used as a replacement solvent for chemical syntheses for tetrahydrofuran (referred to hereinafter as THF), from which it differs advantageously by its lower water solubility which decreases with increasing temperature, as a fuel additive since it is better miscible with common hydrocarbon-based fuels than alcoholic additives, and as a comonomer for the preparation of polyethers with improved properties over the homopolymers.

2-Me-THF is obtainable from renewable raw materials. 2-Me-THF can be obtained from plant wastes by digesting the hemicelluloses present to give furfural and converting it to 2-Me-THF, and thus contributes to sustainable development.

While the preparation of furfural from plant wastes, especially agricultural wastes, is known and has achieved a high level of development, the conversion of furfural to 2-Me-THF, in contrast, is yet to be solved in a technically satisfactory manner.

The elementary reactions of the hydrogenating conversion of furfural are known and have been described in detail by Zheng et al., Journal of Molecular Catalysis A: Chemical (2006), 246 (1-2), 18-23. The authors consider 2-methylfuran to be necessary as a precursor in the preparation of 2-Me-THF and describe main reactions and side reactions of the hydrogenation, including the formation of carbon monoxide by decarbonylation.

Even though 2-Me-THF frequently forms in small amounts in hydrogenating conversions of furfural, there are only few publications in which the direct conversion of furfural to 2-Me-THF is described.

Kyosuke et al., J. Pharm. Soc. Jpn 66 (1946), 58 show that the direct conversion of furfural to 2-methyl-THF over Raney nickel catalysts at 260° C. affords only small amounts of the product of value. Instead, Kyosuke et al. recommend as advantageous a two-stage process via methylfuran as an isolated intermediate and the use of various catalysts for the two stages. For instance, copper chromite according to Adkins is used in the first stage and Raney nickel in the second stage.

Proskuryakov et al., Trudy Leningradskogo Tekhnologicheskogo Instituta imeni Lensoveta (1958), 44, 3-5, describe a yield of not more than 42% 2-Me-THF in the conversion of furfural over a 1:1 mixture of a Raney nickel catalyst and a copper chromite catalyst in an autoclave at 220° C, and 160 atm. The authors show that higher 2-Me-THF contents cannot be obtained by this route owing to side reactions to give glycols and other ring-opening products of furfural not specified in detail.

Another disadvantage which has been recognized is the difficult isolation and purification of 2-Me-THF from the resulting reaction effluent mixtures, since the THF, 2-pentanone and water by-products, as pure substances or in the form of their azeotropes, have boiling points similar to that of 2-Me-THF. For instance, the boiling point of the water/2-Me-THF azeotrope is 73° C., that of the water/THF azeotrope is 64° C. and that of the water/2-pentanone azeotrope is 84° C., while the pure substance THF boils at 66° C., the pure substance 2-Me-THF boils at 80° C. and the pure substance 2-pentanone boils at 102° C.

U.S. Pat. No. 6,479,677 discloses a two-stage process for preparing 2-Me-THF using a separate catalyst in each case for each stage. Each stage is performed in a separate reactor with different catalysts. This gas phase process comprises the hydrogenation of furfural over a copper chromite catalyst to give methylfuran, which is then converted to 2-Me-THF over a nickel catalyst.

However, the process disclosed has a series of disadvantages. For instance, different reaction conditions are required for the individual stages of the reaction, which complicates the industrial performance and necessitates spatial separation of the individual reactors. The addition of hydrogen is required separately for each hydrogenation step, and a large hydrogen excess, as often desired in gas phase reactions, is not tolerated. Furthermore, the formation of carbon monoxide, which always proceeds in small amounts from furfural under thermal stress, leads to deactivation of the nickel catalyst and to the formation of highly toxic, volatile $Ni(CO)_4$. As a result of the accumulation of critical impurities such as carbon monoxide, the economically desirable cycle gas method becomes impossible.

It was therefore an object of the present invention to provide a process for one-stage preparation of 2-methyltetrahydrofuran from furfural using specific catalysts without isolation or purification of intermediates, with whose aid 2-methyltetrahydrofuran can be obtained especially by conversion in a reactor and in circulation mode in good yield and purity.

Accordingly, the present invention relates to a process for one-stage hydrogenation of furfural with a hydrogen-comprising gas in the presence of a structured bed of at least one copper catalyst and at least one catalyst which comprises at least one noble metal from groups 8, 9 and/or 10 of the periodic table of the elements applied on a support material.

In a preferred embodiment, the present invention relates to a process for one-stage hydrogenation of furfural with a hydrogen-comprising gas in the presence of two catalysts, the first comprising a copper catalyst and the second catalyst, as an active metal, at least one noble metal from groups 8, 9, 10 of the periodic table of the elements, especially ruthenium, rhodium, iridium, gold, palladium and/or platinum, preferably palladium and/or platinum, applied on a support material, in a structured bed.

In this application, one-stage or one-stage hydrogenation is understood to mean a process which, proceeding from furfural, without isolation or purification of intermediates, leads to the 2-Me-THF end product.

The first catalyst of the preferred embodiment refers to the catalyst with which the stream of the starting materials, the furfural and the hydrogen-containing gas, comes into contact first on entry into the reactor, while the second catalyst in flow direction is arranged spatially downstream of the first catalyst and is therefore not flowed through until after it.

First Catalyst

The first catalyst is a copper catalyst which preferably, as well as copper, has additional active metals, comprises one or more elements from groups 2, 6 and/or 12 of the periodic table of the elements (new IUPAC nomenclature), especially chromium, manganese, zinc, barium. The total content of the aforementioned active metals is 10-100% by weight, preferably 15-80% by weight, calculated as the oxide. The copper content of the catalyst is at least 10% by weight, calculated as the oxide, but preferably at least 15% by weight, more preferably from 15 to 80% by weight.

Useful first catalysts include unsupported catalysts in which the catalytically active metals are present without support materials, corresponding to an active metal content of 100% by weight, and precipitated catalysts or supported catalysts.

A preferred unsupported catalyst is the catalyst of the composition 24-26% by weight of copper oxide, 1% by weight of chromium(VI) oxide, 1% by weight of chromium(III) oxide, 0-4% by weight of graphite, 65-67% of copper chromite, which is sold as catalyst E 403-TU by Engelhard, Iselin USA.

Precipitated catalysts can be prepared by precipitating their catalytically active components out of their salt solutions, especially out of the solutions of their nitrates and/or acetates, for example by adding solutions of alkaline metal hydroxide and/or alkali metal carbonate and/or alkali earth metal hydroxide and/or alkaline earth metal carbonate solutions, for example as sparingly soluble hydroxides, oxide hydrates, basic salts or carbonates, then drying the resulting precipitates and converting them by calcination at generally from 300 to 700° C., especially from 400 to 600° C., to the corresponding oxides, mixed oxides and/or mixed-valency oxides, which are reduced by a treatment with hydrogen or with hydrogen-comprising gases at generally from 50 to 700° C., especially from 100 to 400° C., to the metals in question and/or oxidic compounds of lower oxidation state and converted to the actual, catalytically active form. In general, reduction is continued until no further water is formed. In the preparation of precipitated catalysts which comprise a support material, the catalytically active components can be precipitated in the presence of the support material in question. The catalytically active components may advantageously, though, also be precipitated simultaneously with the support material from the salt solutions in question. In the process according to the invention, preference is given to using hydrogenation catalysts which comprise metals or metal compounds which catalyze the hydrogenation deposited on a support material.

Apart from the abovementioned precipitated catalysts which, apart from the catalytically active components, also additionally comprise a support material, suitable catalysts for the process according to the invention are generally also supported catalysts, in which the components having catalytically hydrogenating action have been applied to a support material, for example by impregnation.

The way in which the catalytically active metals are applied to the support is generally not critical and it can be accomplished in various ways. The catalytically active metals can be applied to the support materials, for example, by impregnation with solutions or suspensions of the salts or oxides of the elements in question, drying and subsequent reduction of the metal compounds to give the metals or compounds of lower oxidation state in question by means of a reducing agent, preferably with hydrogen or complex hydrides. Another means of applying the catalytically active metals to these supports consists in impregnating the supports with solutions of thermally readily decomposable salts, for example with nitrates, or thermally readily decomposable complexes, for example carbonyl or hydride complexes of the catalytically active metals, and heating the impregnated supports thus obtained to temperatures of from 300 to 600° C. for the purpose of thermal decomposition of the adsorbed metal compounds. This thermal decomposition is preferably undertaken under a protective gas atmosphere. Suitable protective gases are, for example, nitrogen, carbon dioxide, hydrogen or the noble gases. In addition, the catalytically active metals can be deposited on the catalyst support by vapor deposition or by flame-spraying. The content in these supported catalysts of the catalytically active metals is in principle not critical for the success of the process according to the invention. However, higher contents of catalytically active metals generally lead to higher space-time yields than lower contents.

In general, supported catalysts whose content of catalytically active metals, calculated as the oxide, is from 10 to 90% by weight, preferably from 15 to 80% by weight, based on the overall catalyst, are used. Since these content data are based on the overall catalyst including support material, but the different support materials have very different specific weights and specific surface areas, the contents may also be lower or higher than these data, without this having a disadvantageous effect on the result of the process according to the invention. It will be appreciated that it is also possible for a plurality of the catalytically active metals to be applied on the particular support material.

Both the precipitated catalysts and supported catalysts can also be activated in situ at the start of the reaction by the hydrogen present, but these catalysts are preferably activated separately before they are used.

The support materials used may generally be the oxides of aluminum, zirconium dioxide, silicon dioxide, magnesium and calcium oxide. It will be appreciated that mixtures of different support materials may also serve as the support for heterogeneous catalysts useable in the process according to the invention. An example of a first catalyst useable in the process according to the invention is as follows: 25% by weight of copper oxide, 1% by weight of $Cr_2O_3$ and 74% by weight of $SiO_2$.

Second Catalyst

The second catalyst used in accordance with the invention has, as an active metal, at least one noble metal from groups 8, 9, 10 of the periodic table of the elements, especially ruthenium, rhodium, iridium, gold, palladium and/or platinum, preferably palladium and/or platinum, more preferably palladium, on a support. The second catalyst may additionally comprise metals from groups 1, 2, 4 and 7 to 12 of the periodic table of the elements. The elements of groups 1 and 2 of the periodic table of the elements used may especially be sodium, potassium, calcium or magnesium. It preferably does not have any further active metals apart from palladium and platinum.

The application of the active metals can be achieved by impregnating the support in aqueous metal salt solutions, for example aqueous palladium salt solutions, by spraying corresponding metal salt solutions onto the support or by other suitable processes. Suitable metal salts of platinum and palladium are the nitrates, nitrosylnitrates, halides, carbonates, carboxylates, acetylacetonates, chlorides, chloro complexes or amine complexes of the corresponding metals, preference being given to the nitrates.

In the case of catalysts which comprise palladium and platinum and possibly further active metals on the support, the metal salts or metal salt solutions can be applied simultaneously or successively.

The supports coated or impregnated with the metal salt solution are subsequently dried, preferably at temperatures between 100° C. and 150° C., and optionally calcined at temperatures between 200° C. and 600° C., preferably between 350° C. and 450° C. In the case of separate impregnation, the catalyst is dried after each impregnation step and optionally calcined as described above. The sequence in which the active components are applied by impregnation is freely selectable.

Subsequently, the coated and dried and optionally calcined supports are activated by treatment in a gas stream which comprises free hydrogen at temperatures between about 30°

C. and about 600° C., preferably between about 150° C. and about 450° C. The gas stream preferably consists of from 50 to 100% by volume of $H_2$ and from 0 to 50% by volume of $N_2$.

The metal salt solution or solutions is/are applied to the support or supports in such an amount that the total content of active metal, based in each case of the total weight of the catalyst, is from about 0.1 to about 30% by weight, preferably from about 0.1 to about 10% by weight, more preferably from about 0.25 to about 5% by weight, and especially from about 0.5 to about 2.5% by weight.

Useable support metals include, for example, activated carbon, for example in the form of the commercial product Supersorbon carbon from Donau Carbon GmbH, 60388 Frankfurt am Main, aluminum oxide, silicon dioxide, silicon carbide, calcium oxide, titanium dioxide and/or zirconium dioxide or mixtures thereof, preference being given to using activated carbon.

The Process

The process according to the invention features a structured bed of the first and second catalyst.

The inventive one-stage hydrogenation can be performed in one or more, especially two, three, four, five, six, seven, eight, reactors. In the case of use of a plurality of reactors, the first catalyst may be disposed in a first reactor or in a first group of at least two reactors, and the bed of the second catalyst is disposed in the second reactor or in the second group of at least two reactors. However, preference is given to performing the one-stage hydrogenation in one reactor.

The reaction mixture preferably flows through the reactor or the reactors in each case from the top downward. In the case of use of one reactor and correspondingly in the case of use of a plurality of reactors, the first catalyst (copper catalyst) is used for from 20 to 80% of the total height of the catalyst bed, preferably the upper 40 to 60% of the total height of the bed downstream of the top of the single reactor or of the first reactor. The remaining bed height is then formed by the second catalyst (palladium and/or platinum catalyst). When the reactor or the reactors is/are flowed through from the bottom upward, the catalysts are arranged in the reverse sequence.

In the case of use of an individual reactor, it may be advantageous to separate the part of the bed formed from the first catalyst from the part formed from the second catalyst by the introduction of an intermediate layer of inert material. Suitable intermediate separating layers are, for example, glass rings or metal rings. The hydrogenation of the furfural to the 2-Me-THF can therefore be performed advantageously in one stage in one reactor.

In the process according to the invention, the hydrogenation can be performed in the gas phase or the liquid phase; preference is given to working in the gas phase. In general, the process is performed in the gas phase at a temperature of from about 150 to 250° C., preferably from about 190 to 230° C. The pressures used are generally from 1 to 10 bar absolute, preferably from about 1 to 3 bar abs. The pressure in this application is reported as the total pressure or absolute (abs.) pressure.

In the liquid phase, the process according to the invention is performed generally at from 150 to 250° C. at pressures of from 1 to 250 bar abs., preferably at from 20 to 200 bar abs.

In addition to the copper catalyst and the noble metal catalyst which are required to perform the process according to the invention and are referred to as first and second catalyst, it is possible for further catalysts to be present in the reactor or in the reactors. These catalysts may serve, for example, to improve the product quality by removing impurities or converting by-products. For example, sulfur-containing components which are generally present in a small amount in furfural can be removed by treatment with desulfurization catalysts or adsorbents based on copper and/or molybdenum oxides and/or zinc oxides. A by-product obtained when working with furfural is always small amounts of carbon monoxide. This by-product may, for example, be converted to methanol by hydrogenating over copper and/or ruthenium catalysts and thus be removed; it is analogously possible to convert ketonic and aldehydic by-products to alcohols. Catalysts which fulfill these and similar functions may, in addition to the catalysts necessarily required for the performance of the process according to the invention, be disposed at any point in the reactor. They may be installed upstream of the copper catalyst, or else downstream of the noble metal catalyst, or else between the two catalysts. It is likewise conceivable to use such catalysts in homogeneous mixture, provided that this does not override the structured bed of the copper catalyst and of the noble metal catalyst.

The process according to the invention can be performed either continuously or batchwise, preference being given to the continuous performance of the process. In the continuous process, the amount of furfural for the hydrogenation is from about 0.05 to about 3 kg per liter of catalyst per hour, more preferably from about 0.1 to about 1 kg per liter of catalyst per hour.

The hydrogenation gases used may be any gases which comprise free hydrogen and do not comprise harmful amounts of catalyst poisons, for example CO. For example, it is possible to use reformer offgases. Preference is given to using pure hydrogen as the hydrogenation gas. However, it is also possible additionally to use inert carrier gases such as steam or nitrogen.

Molar Hydrogen/Furfural Ratio

The mixing ratio of hydrogen and furfural is not critical provided that sufficient amounts of hydrogen (4 equivalents) are available for the conversion of furfural to 2-methyl-THF. An excess of hydrogen is possible. In the continuous process, the hydrogen/furfural ratio at the reactor inlet is from 4:1 to 500:1, preferably from 5:1 to 250:1, more preferably from 10:1 to 100:1.

In the liquid phase, the inventive hydrogenation can be performed in the absence or presence of a solvent or diluent, i.e. it is not necessary to perform the hydrogenation in solution.

However, it is possible to use a solvent or diluent. The solvent or diluent used may be any suitable solvent or diluent. The selection is not critical provided that the solvent or diluent used is capable of forming a homogeneous solution with the furfural to be hydrogenated.

Examples of suitable solvents or diluents include the following: straight-chain or cyclic ethers, for example tetrahydrofuran or dioxane, and aliphatic alcohols in which the alkyl radical preferably has from 1 to 10 carbon atoms, especially from 3 to 6 carbon atoms.

The amount of the solvent or diluent used is not particularly restricted and may be selected freely as required, although preference is given to those amounts which lead to from 10 to 70% by weight solution of the furfural intended for the hydrogenation.

Furthermore, the hydrogenation reactor, in the case of performance of the hydrogenation in the liquid phase, can be operated in straight pass, i.e. without product recycling, or in circulation, i.e. a portion of the hydrogenation mixture leaving the reactor is conducted in a circuit.

In the case of performance of the inventive hydrogenation in the gas phase, the reaction products are condensed fully and removed after leaving the reactor. The gaseous fractions, hydrogen and any additional carrier gas used are returned partly to the reactor in circulation (cycle gas mode). In the preferred cycle gas mode, the ratio of cycle gas to fresh gas volumes is at least 1:1, preferably at least 5:1, more preferably at least 10:1.

Useful reactors include fixed bed reactors, for example tube bundle reactors. The selection of the reactor type is not critical per se provided that the catalyst arrangement in the bed, i.e. the sequence in which the reaction mixture flows through the catalysts, is not changed. In the liquid method, it is possible to use fluidized bed reactors when the beds of the two catalyst types are arranged such that mixing of the first and second catalyst in the course of operation of the reactor is ruled out.

The reaction effluents of the inventive hydrogenation are condensed in a manner known per se, but preferably by cooling in a heat exchanger to from 0 to 80° C. After the condensation, a phase separation sets in. The lower phase consists of water to an extent of more than 90%, while the upper phase, as well as the desired 2-Me-THF product, comprises only small amounts of by-products which can be removed readily by any subsequent purifying distillation. 2-Methyltetrahydrofuran (2-Me-THF) is obtained by the process according to the invention in very good purity and yield. The phase separation can be effected at ambient temperature. However, the reaction effluents are preferably condensed at 60° C. since the miscibility of 2-methyl-THF and water is particularly low at this temperature.

The process according to the invention will now be illustrated in detail hereinafter with reference to a few working examples.

EXAMPLES

Catalyst Preparation Example 4 kg of Supersorbon carbon (4 mm extrudates, manufacturer: Donau Carbon GmbH) were initially charged in an impregnating drum and sprayed with 2.8 kg of a 7.2% by weight aqueous solution of palladium(II) nitrate, based on palladium, at room temperature with the aid of a fine nozzle (1 mm). The liquid was absorbed completely into the pores of the carbon support. The material was subsequently dried in a drying cabinet at 100° C. for 40 hours.

Subsequently, the dried catalyst was activated (reduced) in a water stream at 200° C. The catalyst thus prepared comprised 5% by weight of palladium based on the weight of the catalyst.

Analysis of the Hydrogenation Products

The 2-Me-THF, 2-pentanone, 3-pentanone, 1-pentanol, THF, furan and methylfuran reaction products and the furfural starting material were analyzed by gas chromatography. To this end, the mixtures were injected, diluted with methanol or acetone (dilution of from 1:10 to 1:100) or undiluted, into the GC chromatograph (from HP, carrier gas: hydrogen) onto a 30 m DB1 column (from J+W) and analyzed at oven temperatures of from 60° C. to 300° C. (heating rate 8 Kelvin per minute up to 220° C., then 20 Kelvin per minute up to 300° C.) with a flame ionization detector (temperature: 290° C.). The purity was determined by integrating the signals of the chromatogram.

Example 1

In a system for continuous hydrogenation consisting of an evaporator, an oil-heated 3.8 l jacketed tubular reactor and a separator and a cycle gas compressor, furfural was hydrogenated continuously over fixed bed catalysts in the gas phase.

The tubular reactor was filled with 450 g of a Pd catalyst (5% Pd/Supersorbon carbon, 4 mm extrudates), then at the top with 530 g of the copper chromite catalyst E 403-TU from Engelhard Iselin; USA, now BASF (24-26% by weight of copper oxide, 1% by weight of chromium(VI) oxide, 1% by weight of chromium(III) oxide, 0-4% by weight of graphite, 65-67% by weight of copper chromite, 3 mm×3 mm tablets).

The tubular reactor was flowed through from the top downward. The catalysts were activated with nitrogen/hydrogen mixtures at 200° C. at ambient pressure by the method known to those skilled in the art such that the content of hydrogen in the mixed gas was increased slowly from 0 up to 100%. Subsequently, the system was pressurized to 4 bar with hydrogen, fresh hydrogen gas was adjusted to 450 l (STP/h), the evaporator was heated to 230° C., the reactor to 220° C., and the cycle gas was put into operation. 400 g/h of furfural which had been distilled in one stage were conveyed into the evaporator. During the hydrogenation, the cycle gas was adjusted to 240 g/h, 83 l (STP/h) of offgas were sent to incineration. Under these conditions, over 440 h, furfural was converted to an extent of >99%; the selectivity for 2-MeTHF was >80%. The upper phase of the biphasic effluent had the following composition: furan, 2-methylfuran, THF each <0.5% by weight, 2-MeTHF 84% by weight, 2-pentanone 2.4% by weight, 2-pentanol 1.3% by weight, 1-pentanol 4% by weight, methyl-gamma-butyrolactone 5% by weight, remainder to 100% unidentified by-products. The by-products could be removed by means of distillation according to the prior art, such that the desired 2-MeTHF was obtained in a purity of >99%.

Example 2

In an electrically heatable, vertically installed quartz tube as a reactor (internal diameter 2.5 cm, length 60 cm), 50 ml (21 g) of a palladium-carbon catalyst according to example 1 (5% Pd of Supersorbon-K, 4 mm extrudates) were blanketed with 10 ml of quartz glass rings (to separate the catalyst layers) and 50 ml (30 g) of a copper chromite catalyst E 403-TU from Engelhard Iselin; USA (24-26% by weight of copper oxide, 1% by weight of chromium(VI) oxide, 1% by weight of chromium(III) oxide, 0-4% by weight of graphite, 65 to 67% by weight of copper chromite, 3 mm×3 mm tablets) and covered with a further 100 ml of quartz glass rings (as an evaporation zone).

The quartz tube with this structured catalyst/quartz glass ring bed was provided with a gas feed tube and a liquid feed tube and installed such that the reaction products were condensed and collected in a helical glass condenser. The reactor was flowed through from the top downward, i.e. the reaction mixture flowed first through the copper chromite catalyst, then through the Pd catalyst.

The catalysts were activated by treatment with hydrogen, initially diluted in a nitrogen stream, later in pure form, in each case at ambient pressure at 200° C. for 2 h. 5 ml/h (approx. 5.8 g/h) of furfural were then converted at a hydrogen flow of 15 l/h and reactor temperatures of a) 175, b) 200, c) 225 and d) 250° C. and ambient pressure. The conversion of the reactant (furfural) was complete at all aforementioned temperatures a) to d). The reaction effluents were condensed and, after the condensation, the reaction effluent started to separate into two phases. The lower phase, about <⅕ of the total amount of the particular reaction effluent, consisted of water to an extent of >90% and was discarded. Depending on the reaction temperature, the upper phase had the following compositions determined by gas chromatography:

TABLE 1

| Ex. | T °C. | 2-Me-THF % by wt. | 2-Pentanone | 3-Pentanone | 1-Pentanol | THF | Methyl-furan | Furan |
|---|---|---|---|---|---|---|---|---|
| 2 a | 175 | 91 | 0.5 | <0.5 | 2 | <0.5 | <0.5 | <0.5 |
| 2 b | 200 | 91 | 2 | 1 | 2 | 1 | <0.5 | <0.5 |
| 2 c | 225 | 86 | 4 | 2 | 1 | 2 | <0.5 | 1 |
| 2 d | 250 | 82 | 5 | <0.5 | 1 | 4 | 0.5 | 0.5 |

In addition to the organic fractions, the upper phases of the effluents additionally comprised from 2 to 8% water.

The upper phase, which comprised the 2-Me-THF reaction product, was distilled in a column with random packing of length 1.2 m, an internal diameter of 2.5 cm with 3×3 mm V2A metal rings as random packings, and the 2-Me-THF product was obtained in >99% purity.

Example 3

Analogously to example 2, a copper catalyst with a mineral support (composition in the unactivated state 25% CuO/1%$Cr_2O_3$/74% $SiO_2$) and a palladium-carbon catalyst (5% Pd on Supersorbon-K, 4 mm extrudates) was installed into the reactor. At 225° C., the following composition of the reaction effluent was obtained:

85% 2-Me-THF, 5% 2-pentanone, <0.5% 3-pentanone, <0.5% 1-pentanol, 1% 2-pentanol, 4% THF, 0.5% furan, <0.5% methylfuran and further unidentified products.

Example 4

Analogously to example 2, 24.2 g of a copper catalyst with a mineral support of the composition in the unactivated state of 25% CuO/1%$Cr_2O_3$/74% $SiO_2$ and 28.1 g of a platinum-carbon catalyst (5% Ptd on 4 mm Supersorbon K extrudates) were installed into the reactor. At 225° C., the following composition of the reaction effluent was obtained: 82% 2-Me-THF, 4% 2-pentanone, 1% 3-pentanone, <0.5% 1-pentanol, 1% 2-pentanol, 3% THF, 0.5% furan, 1% methylfuran and further unidentified products.

The invention claimed is:

1. A process, comprising:
    hydrogenating furfural with a hydrogen-comprising gas in the presence of a structured bed comprising a first catalyst comprising copper and a second catalyst comprising at least one noble metal selected from the group consisting of a group 8, a group 9, and a group 10 element of the periodic table, to obtain 2-methyltetrahydrofuran,
    wherein the second catalyst is comprised on a support material, and
    wherein the hydrogenating is carried out in one stage.

2. The process of claim 1, wherein the hydrogenating is effected in the presence of the first and the second catalysts in the structured bed.

3. The process of claim 2, wherein a stream comprising the furfural and the hydrogen-comprising gas flows first through the first catalyst and then through the second catalyst.

4. The process to of claim 2, wherein the structured bed comprising the the first and second catalysts is arranged in a reactor.

5. The process of claim 1, wherein the first catalyst further comprises at least one element of the periodic table selected from the group consisting of a group 2, a group 6, and a group 12 element.

6. The process of claim 2, wherein the first catalyst further comprises at least one element selected from the group consisting of chromium, manganese, zinc, and barium.

7. The process to of claim 2, wherein the first catalyst has a copper content of at least 10% by weight.

8. The process of claim 2, wherein the second catalyst comprises at least one element selected from the group consisting of palladium and platinum.

9. The process of claim 8, wherein the second catalyst comprises from 0.1 to 30% by weight of at least one element selected from the group consisting of palladium and platinum on the support material.

10. The process of claim 8, wherein the second catalyst further comprises at least one element of the periodic table selected from the group consisting of a group 1, a group 2, a group 4, and a group 7 to 12 element on the support material.

11. The process to of claim 8, wherein the support material comprises at least one material selected from the group consisting of activated carbon, aluminum oxide, silicon dioxide, silicon carbide, calcium oxide, titanium dioxide, and zirconium dioxide.

12. The process of claim 1, wherein the first catalyst forms from 20 to 80% of a total height of the structured bed downstream of a top of a reactor.

13. The process of claim 1, wherein the hydrogenating is performed in the liquid phase at a temperature of from 150 to 250° C. and a pressure of from 20 to 200 bar absolute.

14. The process of claim 13, wherein the hydrogenating is performed in the presence of a solvent.

15. The process of claim 1, wherein the hydrogenating is performed in the gas phase at a temperature of from 150 to 250° C. and a pressure of from 1 to 10 bar absolute.

16. The process of claim 1, wherein the hydrogenating is performed in a cycle gas or a circulation mode.

17. The process of claim 13, wherein the hydrogenating is performed in the absence of a solvent.

18. The process of claim 2, wherein the first catalyst has a copper content of at least 15% by weight.

19. The process of claim 2, wherein the first catalyst has a copper content of from 15% to 80% by weight.

20. The process of claim 15, further comprising, after the hydrogenating,
    condensing an effluent comprising the 2-methyltetrahydrofuran, to obtain a lower phase having a water content of at least 90% and an upper phase having a 2-methyltetrahydrofuran content of at least 82%.

* * * * *